(12) United States Patent
Maasalo

(10) Patent No.: US 11,982,666 B2
(45) Date of Patent: May 14, 2024

(54) SYSTEM AND METHOD FOR THE REAL-TIME MONITORING AND PREDICTION OF CONCRETE DRYING

(71) Applicant: Lari Maasalo, Tampere (FI)

(72) Inventor: Lari Maasalo, Tampere (FI)

(73) Assignee: eGate Smart Building Innovation Oy, Ylöjärvi (FI)

( * ) Notice: Subject to any disclaimer, the term of this patent is extended or adjusted under 35 U.S.C. 154(b) by 269 days.

(21) Appl. No.: 17/722,716

(22) Filed: Apr. 18, 2022

(65) Prior Publication Data

US 2023/0333081 A1 Oct. 19, 2023

(51) Int. Cl.
| | |
|---|---|
| *G01N 33/00* | (2006.01) |
| *G01N 27/04* | (2006.01) |
| *G01N 33/38* | (2006.01) |
| *G06F 18/21* | (2023.01) |

(52) U.S. Cl.
CPC ......... *G01N 33/383* (2013.01); *G01N 27/048* (2013.01); *G06F 18/217* (2023.01)

(58) Field of Classification Search
CPC ... G01N 33/383; G01N 27/048; G06F 18/217
See application file for complete search history.

(56) References Cited

U.S. PATENT DOCUMENTS 10,126,288 B2 * 11/2018 Radjy .................. G01N 33/383

\* cited by examiner

*Primary Examiner* — Jamel E Williams
(74) *Attorney, Agent, or Firm* — The Repacke Law Group, P.A.; Andrew S. Rapacke

(57) ABSTRACT

A system and method for the real-time monitoring and updating of a prediction of concrete drying is disclosed. The system includes one or more sensors positioned inside a concrete slab and one or more sensors positioned outside the concrete slab. Each sensor positioned inside and outside the concrete slab to transmit data to a cloud-based web portal configured to transmit a prediction to a computing device.

17 Claims, 3 Drawing Sheets

SYSTEM AND METHOD FOR THE REAL-TIME MONITORING AND PREDICTION OF CONCRETE DRYING

CROSS-REFERENCE TO RELATED APPLICATIONS

The present application claims priority to U.S. Provisional Patent Application No. 63/175,272 filed Apr. 15, 2021, entitled "SYSTEM AND METHOD FOR THE REAL-TIME MONITORING AND PREDICTION OF CONCRETE DRYING" which is hereby incorporated by reference in its entirety.

TECHNICAL FIELD

The embodiments generally relate to systems and methods for the real-time prediction and monitoring of concrete drying.

BACKGROUND

Moisture problems in building construction and floor installation often occur when impermeable flowing is installed over the top of a concrete slab which has not properly dried. Small temperature changes may cause the water molecules trapped below the surface to condense, causing damage such as blistering, debonding, and warping. Variabilities include time, ambient relative humidity, slab thickness, temperature, weather patterns, and the like.

In today's building construction industry, a typical method in estimating the drying time of a fresh concrete floor, is to use rules of thumb estimates (e.g., 30-days per inch of slab thickness), prior experience, or to periodically measure concrete moisture with sensors and manually update forecasting formulas. This often leads to project scheduling errors that can result in significant cost in lost time and money.

SUMMARY OF THE INVENTION

This summary is provided to introduce a variety of concepts in a simplified form that is disclosed further in the detailed description of the embodiments. This summary is not intended to identify key or essential inventive concepts of the claimed subject matter, nor is it intended for determining the scope of the claimed subject matter.

The embodiments provided herein relate to a system and method for the real-time monitoring and updating of a prediction of concrete drying is disclosed. The system includes one or more sensors positioned inside a concrete slab and one or more sensors positioned outside the concrete slab. Each sensors positioned inside and outside the concrete slab to transmit data to a cloud-based web portal configured to transmit a prediction to a computing device.

In one aspect, an algorithm is operated by the cloud-based web portal to receive the data and calculate the prediction.

In one aspect, the data is comprised of the following: relative temperature inside the concrete slab, relative humidity outside the concrete slab, temperature inside the concrete slab, temperature outside the concrete slab.

In one aspect, the data further comprises a date and a time when the concrete slab was poured, and a target relative humidity value inside the concrete slab.

The algorithm first collects instantaneous relative humidity samples from inside the concrete are filtered by applying a filter. Absolute humidity values in the concrete and in the surrounding air are calculated from the respective relative humidity and temperature values. A non-linear extrapolation curve is applied on the filtered relative humidity values from inside the concrete. This extrapolation is adjusted with a factor calculated from the difference of absolute humidity in the concrete and in the surrounding air. The humidity difference factor is calculated from the average values over a predetermined time period (e.g., 7 days).

BRIEF DESCRIPTION OF THE DRAWINGS

A complete understanding of the present embodiments and the advantages and features thereof will be more readily understood by reference to the following detailed description when considered in conjunction with the accompanying drawings wherein.

DETAILED DESCRIPTION

Figure 1:
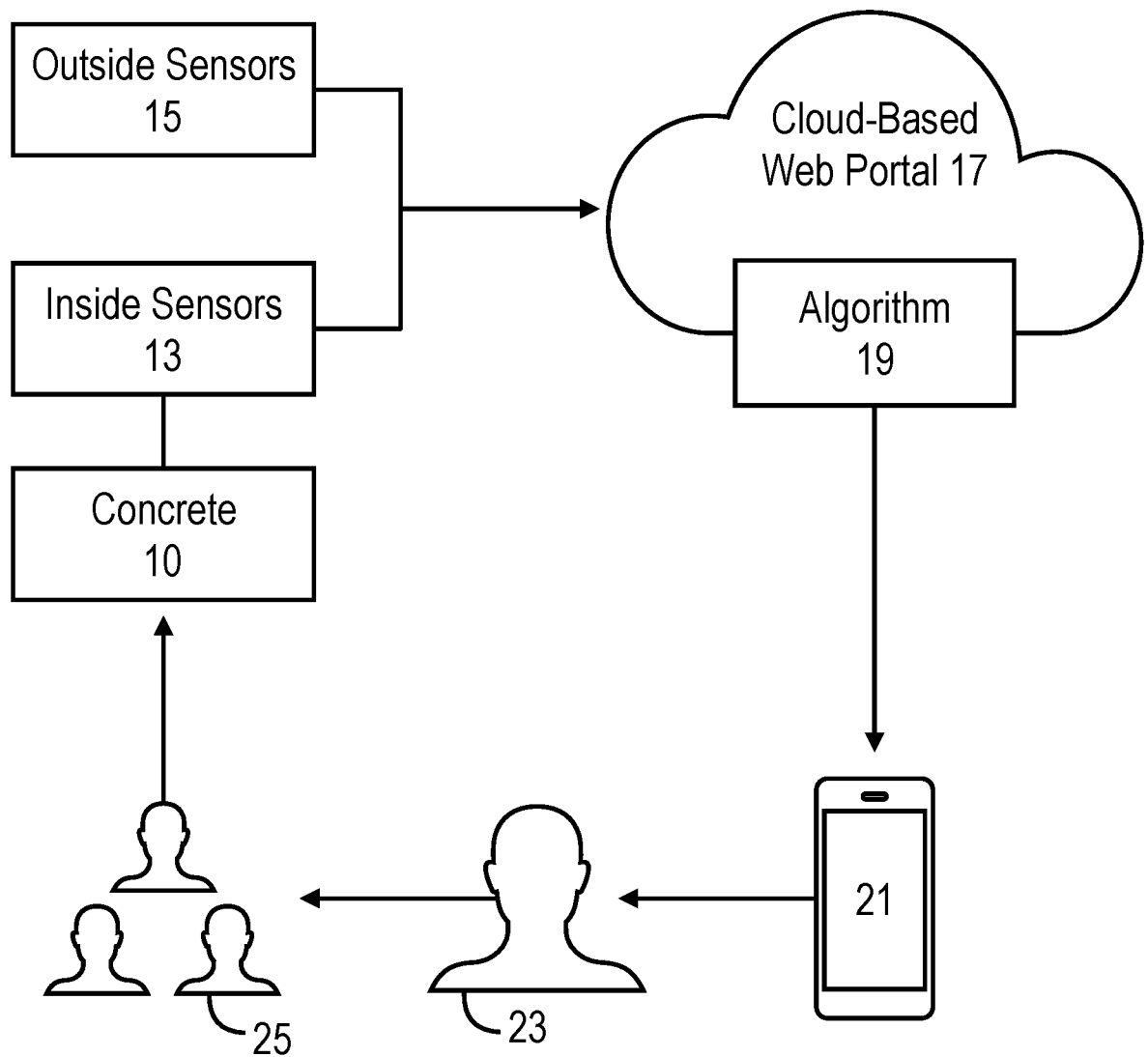
FIG. 1 illustrates a flow diagram of the system for the real-time monitoring and prediction of concrete drying, according to some embodiments.
Figure 2:
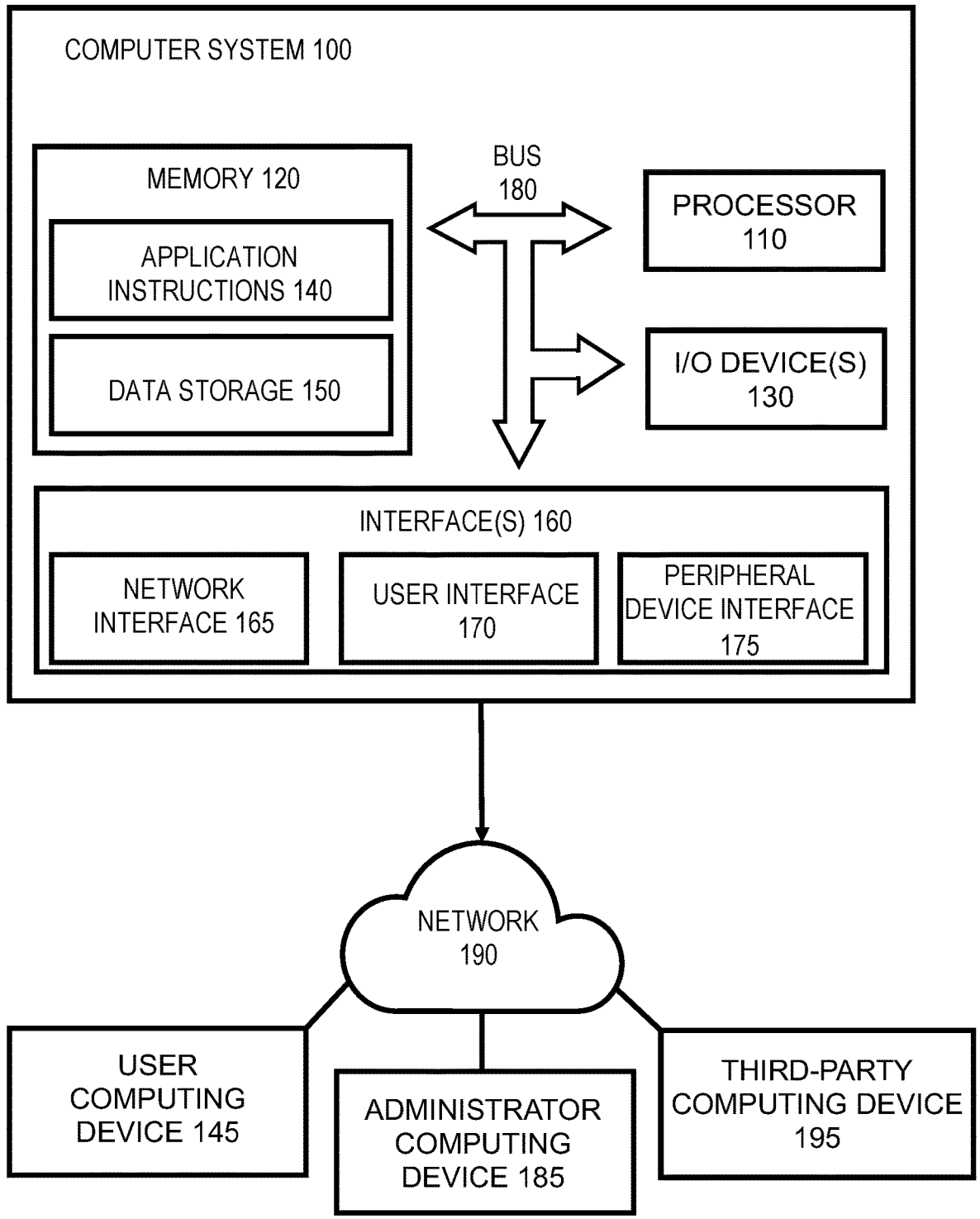
FIG. 2 illustrates a block diagram of the computer system, according to some embodiments.

The specific details of the single embodiment or variety of embodiments described herein are to the described system and methods of use. Any specific details of the embodiments are used for demonstration purposes only, and no unnecessary limitations or inferences are to be understood thereon.

Before describing in detail exemplary embodiments, it is noted that the embodiments reside primarily in combinations of components and procedures related to the system. Accordingly, the system components have been represented, where appropriate, by conventional symbols in the drawings, showing only those specific details that are pertinent to understanding the embodiments of the present disclosure so as not to obscure the disclosure with details that will be readily apparent to those of ordinary skill in the art having the benefit of the description herein.

In this disclosure, the various embodiments may be a system, method, and/or computer program product at any possible technical detail level of integration. A computer program product can include, among other things, a computer-readable storage medium having computer-readable program instructions thereon for causing a processor to carry out aspects of the present disclosure.

In general, the embodiments provided herein relate to an automatically updating concrete drying prediction method and system which is made possible by combining cloud-connected wireless concrete humidity sensors, with prediction algorithms. The system and method combine real-time measurement data received from a plurality of sensors positioned within the concrete slab and in the surrounding environment. The system and method permit the continuous updating of a forecast of the time remaining to reach a predetermined humidity level inside the concrete.

The forecast prediction is not static and will instead react to changes in conditions inside the drying concrete slab and the surrounding environment.

The invention provides the users with a regularly updating prediction of when the monitored concrete structures on construction sites will be dry enough to start with the next construction phases, such as installing a floor mat. The "early warning" will give the users time to better prepare for the next work steps, plan the schedules and allocate the resources needed in good time. This will give clear advantages, in the form of time and cost savings, over the traditional method of regularly visiting the construction sites and sampling the concrete humidity to see if the structures are dry enough to carry on with the work. The invention will also decrease the risk of structural damages caused by excess humidity getting trapped in the concrete due to flooring that was installed too early.

This invention combines the high quality data from wireless IoT sensors inside and outside of the drying concrete that is automatically and regularly collected to the cloud-based web portal with a self-adjusting extrapolation algorithm that outputs a regularly updating prediction of the remaining drying time to reach a desired target humidity level inside the concrete. This prediction is not static and instead will react to changes in conditions inside the drying concrete and the surrounding air.

The sensors located inside and outside of the concrete slab, for continuously measuring the temperature and humidity and automatically updating the concrete drying forecast in the web portal where the results are quickly and easily available. In some embodiments, the sensors may be wireless Internet-of-Things (TOT) sensors capable of remotely communicating with a computing device with which a user may operate.

In some embodiments, the prediction algorithm may not need any manually entered data about the drying concrete structure, like used concrete type, thickness of the structure etc. The prediction algorithm constantly adapts to the changing conditions inside and just outside of the drying concrete and updates the prediction accordingly, without any user action or intervention.

FIG. 1 illustrates a flow diagram of the system which relies on accurate humidity and temperature readings taken regularly from inside the drying concrete 10 and from the surrounding environment. This method combines the data from sensors inside the concrete 13 (i.e., inside sensors) and outside of the concrete 15 (i.e., outside sensors) the concrete that is automatically and regularly transmitted to a cloud-based web portal 17 with a self-adjusting extrapolation algorithm 19 that outputs a regularly updating prediction of the remaining drying time to reach the target humidity level inside the concrete. The output of the prediction is displayed on a computing device 21. Extrapolation curve fitting is controlled by the difference in absolute humidity between the concrete and air. The prediction results are not necessarily monotonous as the algorithm will react to the changes of measured conditions and the prediction can also increase over time.

In some embodiments, the first prediction may not be available right away as the algorithm needs to accumulate data over a sufficiently long time period to base the extrapolation on. Time when the concrete was cast is needed as a reference point for the algorithm. This time can be entered, via a user 23 with the cloud-based web-portal 17 for each prediction point separately. When the predicted remaining drying time reaches a preset target limit, the cloud-based web portal 17 can send the users 23 a message to notify that the concrete is almost dry. This will give the users 23 an early warning and time to prepare for the next construction phase. The user may notify a group 25 to perform the next construction phase.

The system and method may require relative humidity and temperature measure from inside the drying concrete. Measurements of the relative humidity and temperature may be input via the sensors which provide continuous data to the cloud-based prediction algorithm. Further, relative humidity and temperature may be measured from the surrounding environment. The system and method may also require the date and time the concrete was poured, as well as the target relative humidity value inside the concrete.

The algorithm first collects instantaneous relative humidity samples from inside the concrete are filtered by applying a filter. Absolute humidity values in the concrete and in the surrounding air are calculated from the respective relative humidity and temperature values. A non-linear extrapolation curve is applied on the filtered relative humidity values from inside the concrete. This extrapolation is adjusted with a factor calculated from the difference of absolute humidity in the concrete and in the surrounding air. The humidity difference factor is calculated from the average values over a predetermined time period (e.g., 7 days). If the surrounding air has a higher absolute humidity than the concrete, no prediction is given as the concrete ceases to dry in these conditions. If the trend of the relative humidity inside the concrete during the last 7 days is rising, no prediction is given.

The algorithm may output a prediction of remaining time it takes for the relative humidity inside the concrete to decrease to the desired target value. The prediction may be provided to the user in full day increments, or other time increments selected by the user. This is a prediction only that relies on the historical and current conditions, and it can vary significantly from day-to-day if the environmental conditions are not stable.

The algorithm may not always be able to give a prediction. This is always the case in the first days or weeks after the casting when the relative humidity inside the concrete stays fixed at 100% and several days after this. In some embodiments, the algorithm cannot give a prediction if the relative humidity inside the concrete starts to rise continuously or if the absolute humidity in the surrounding air is higher than inside the concrete for a substantial period of time.

FIG. 1 illustrates an example of a computer system 100 that may be utilized to execute various procedures, including the processes described herein. The computer system 100 comprises a standalone computer or mobile computing device, a mainframe computer system, a workstation, a network computer, a desktop computer, a laptop, or the like. The computing device 100 can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive).

In some embodiments, the computer system 100 includes one or more processors 110 coupled to a memory 120 through a system bus 180 that couples various system components, such as an input/output (I/O) devices 130, to the processors 110. The bus 180 may be any of several types of bus structures including a memory bus or memory controller, a peripheral bus, and a local bus using any of a variety of bus architectures. For example, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus, also known as Mezzanine bus.

In some embodiments, the computer system 100 includes one or more input/output (I/O) devices 130, such as video device(s) (e.g., a camera), audio device(s), and display(s) are in operable communication with the computer system 100.

In some embodiments, similar I/O devices 130 may be separate from the computer system 100 and may interact with one or more nodes of the computer system 100 through a wired or wireless connection, such as over a network interface.

Processors 110 suitable for the execution of computer readable program instructions include both general and special purpose microprocessors and any one or more processors of any digital computing device. For example, each processor 110 may be a single processing unit or a number of processing units and may include single or multiple computing units or multiple processing cores. The processor(s) 110 can be implemented as one or more microprocessors, microcomputers, microcontrollers, digital signal processors, central processing units, state machines, logic circuitries, and/or any devices that manipulate signals based on operational instructions. For example, the processor(s) 110 may be one or more hardware processors and/or logic circuits of any suitable type specifically programmed or configured to execute the algorithms and processes described herein. The processor(s) 110 can be configured to fetch and execute computer readable program instructions stored in the computer-readable media, which can program the processor(s) 110 to perform the functions described herein.

In this disclosure, the term "processor" can refer to substantially any computing processing unit or device, including single-core processors, single-processors with software multithreading execution capability, multi-core processors, multi-core processors with software multithreading execution capability, multi-core processors with hardware multithread technology, parallel platforms, and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures, such as molecular and quantum-dot based transistors, switches, and gates, to optimize space usage or enhance performance of user equipment. A processor can also be implemented as a combination of computing processing units.

In some embodiments, the memory 120 includes computer-readable application instructions 150, configured to implement certain embodiments described herein, and a database 150, comprising various data accessible by the application instructions 140. In some embodiments, the application instructions 140 include software elements corresponding to one or more of the various embodiments described herein. For example, application instructions 140 may be implemented in various embodiments using any desired programming language, scripting language, or combination of programming and/or scripting languages (e.g., C, C++, C#, JAVA, JAVASCRIPT, PERL, etc.).

In this disclosure, terms "store," "storage," "data store," data storage," "database," and substantially any other information storage component relevant to operation and functionality of a component are utilized to refer to "memory components," which are entities embodied in a "memory," or components comprising a memory. Those skilled in the art would appreciate that the memory and/or memory components described herein can be volatile memory, nonvolatile memory, or both volatile and nonvolatile memory. Nonvolatile memory can include, for example, read only memory (ROM), programmable ROM (PROM), electrically programmable ROM (EPROM), electrically erasable ROM (EEPROM), flash memory, or nonvolatile random access memory (RAM) (e.g., ferroelectric RAM (FeRAM). Volatile memory can include, for example, RAM, which can act as external cache memory. The memory and/or memory components of the systems or computer-implemented methods can include the foregoing or other suitable types of memory.

Generally, a computing device will also include, or be operatively coupled to receive data from or transfer data to, or both, one or more mass data storage devices; however, a computing device need not have such devices. The computer readable storage medium (or media) can be a tangible device that can retain and store instructions for use by an instruction execution device. The computer readable storage medium can be, for example, an electronic storage device, a magnetic storage device, an optical storage device, an electromagnetic storage device, a semiconductor storage device, or any suitable combination of the foregoing. A non-exhaustive list of more specific examples of the computer readable storage medium can include: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. In this disclosure, a computer readable storage medium is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

In some embodiments, the steps and actions of the application instructions 140 described herein are embodied directly in hardware, in a software module executed by a processor, or in a combination of the two. A software module may reside in RAM, flash memory, ROM memory, EPROM memory, EEPROM memory, registers, a hard disk, a removable disk, a CD-ROM, or any other form of storage medium known in the art. An exemplary storage medium may be coupled to the processor 110 such that the processor 110 can read information from, and write information to, the storage medium. In the alternative, the storage medium may be integrated into the processor 110. Further, in some embodiments, the processor 110 and the storage medium may reside in an Application Specific Integrated Circuit (ASIC). In the alternative, the processor and the storage medium may reside as discrete components in a computing device. Additionally, in some embodiments, the events or actions of a method or algorithm may reside as one or any combination or set of codes and instructions on a machine-readable medium or computer-readable medium, which may be incorporated into a computer program product.

In some embodiments, the application instructions 140 for carrying out operations of the present disclosure can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The application instructions 140 can execute entirely on the user's computer, partly on the user's computer, as a stand-alone software package, partly on the user's computer and partly on a remote computer, or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instructions by utilizing state information of the computer readable program instructions to personalize the electronic circuitry, in order to perform aspects of the present disclosure.

In some embodiments, the application instructions 140 can be downloaded to a computing/processing device from a computer readable storage medium, or to an external computer or external storage device via a network 190. A network adapter card or network interface in each computing/processing device receives computer readable program instructions from the network and forwards the computer readable application instructions 140 for storage in a computer readable storage medium within the respective computing/processing device.

In some embodiments, the computer system 100 includes one or more interfaces 160 that allow the computer system 100 to interact with other systems, devices, or computing environments. In some embodiments, the computer system 100 comprises a network interface 165 to communicate with a network 190. In some embodiments, the network interface 165 is configured to allow data to be exchanged between the computer system 100 and other devices attached to the network 190, such as other computer systems, or between nodes of the computer system 100. In various embodiments, the network interface 165 may support communication via wired or wireless general data networks, such as any suitable type of Ethernet network, for example, via telecommunications/telephony networks such as analog voice networks or digital fiber communications networks, via storage area networks such as Fiber Channel SANs, or via any other suitable type of network and/or protocol. Other interfaces include the user interface 170 and the peripheral device interface 175.

In some embodiments, the network 190 corresponds to a local area network (LAN), wide area network (WAN), the Internet, a direct peer-to-peer network (e.g., device to device Wi-Fi, Bluetooth, etc.), and/or an indirect peer-to-peer network (e.g., devices communicating through a server, router, or other network device). The network 190 can comprise copper transmission cables, optical transmission fibers, wireless transmission, routers, firewalls, switches, gateway computers and/or edge servers. The network 190 can represent a single network or multiple networks. In some embodiments, the network 190 used by the various devices of the computer system 100 is selected based on the proximity of the devices to one another or some other factor. For example, when a first user device and second user device are near each other (e.g., within a threshold distance, within direct communication range, etc.), the first user device may exchange data using a direct peer-to-peer network. But when the first user device and the second user device are not near each other, the first user device and the second user device may exchange data using a peer-to-peer network (e.g., the Internet). The Internet refers to the specific collection of networks and routers communicating using an Internet Protocol ("IP") including higher level protocols, such as Transmission Control Protocol/Internet Protocol ("TCP/IP") or the Uniform Datagram Packet/Internet Protocol ("UDP/IP").

Any connection between the components of the system may be associated with a computer-readable medium. For example, if software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. As used herein, the terms "disk" and "disc" include compact disc (CD), laser disc, optical disc, digital versatile disc (DVD), floppy disk, and Blu-ray disc; in which "disks" usually reproduce data magnetically, and "discs" usually reproduce data optically with lasers. Combinations of the above should also be included within the scope of computer-readable media. In some embodiments, the computer-readable media includes volatile and nonvolatile memory and/or removable and non-removable media implemented in any type of technology for storage of information, such as computer-readable instructions, data structures, program modules, or other data. Such computer-readable media may include RAM, ROM, EEPROM, flash memory or other memory technology, optical storage, solid state storage, magnetic tape, magnetic disk storage, RAID storage systems, storage arrays, network attached storage, storage area networks, cloud storage, or any other medium that can be used to store the desired information and that can be accessed by a computing device. Depending on the configuration of the computing device, the computer-readable media may be a type of computer-readable storage media and/or a tangible non-transitory media to the extent that when mentioned, non-transitory computer-readable media exclude media such as energy, carrier signals, electromagnetic waves, and signals per se.

In some embodiments, the system is world-wide-web (www) based, and the network server is a web server delivering HTML, XML, etc., web pages to the computing devices. In other embodiments, a client-server architecture may be implemented, in which a network server executes enterprise and custom software, exchanging data with custom client applications running on the computing device.

In some embodiments, the system can also be implemented in cloud computing environments. In this context, "cloud computing" refers to a model for enabling ubiquitous, convenient, on-demand network access to a shared pool of configurable computing resources (e.g., networks, servers, storage, applications, and services) that can be rapidly provisioned via virtualization and released with minimal management effort or service provider interaction, and then scaled accordingly. A cloud model can be composed of various characteristics (e.g., on-demand self-service, broad network access, resource pooling, rapid elasticity, measured service, etc.), service models (e.g., Software as a Service ("SaaS"), Platform as a Service ("PaaS"), Infrastructure as a Service ("IaaS"), and deployment models (e.g., private cloud, community cloud, public cloud, hybrid cloud, etc.).

As used herein, the term "add-on" (or "plug-in") refers to computing instructions configured to extend the functionality of a computer program, where the add-on is developed specifically for the computer program. The term "add-on data" refers to data included with, generated by, or organized by an add-on. Computer programs can include computing instructions, or an application programming interface (API) configured for communication between the computer program and an add-on. For example, a computer program can be configured to look in a specific directory for add-ons developed for the specific computer program. To add an add-on to a computer program, for example, a user can download the add-on from a website and install the add-on in an appropriate directory on the user's computer.

In some embodiments, the computer system 100 may include a user computing device 145, an administrator computing device 185 and a third-party computing device 195 each in communication via the network 190. The user computing device 145 may be utilized by a user to interact with the various functionalities described herein. The administrator computing device 185 is utilized by an administrative user to moderate content and to perform other administrative functions. The third-party computing device 195 may include any third-party in communication with the system.

Figure 3:
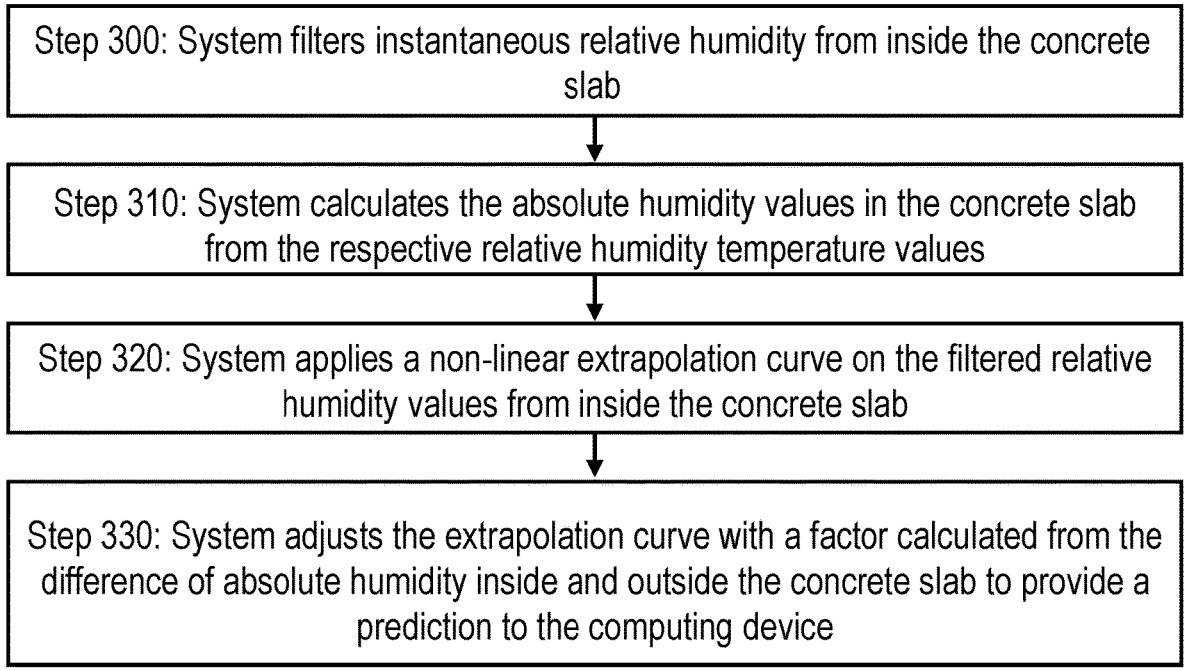
FIG. 3 illustrates a flowchart of a method for the real-time monitoring and updating of a prediction of concrete drying, according to some embodiments.

FIG. 3 illustrates a flowchart of a method for the real-time monitoring and updating of a prediction of concrete drying. In step 300, the system filters instantaneous relative humidity from inside the concrete slab. In step 310, the system calculates the absolute humidity values in the concrete slab from the respective relative humidity and temperature values. In step 320, the system applies a non-linear extrapolation curve on the filtered relative humidity values from inside the concrete. In step 330, the system adjusts the extrapolation curve with a factor calculated from the difference of absolute humidity inside and outside the concrete slab to provide a prediction to the computing device.

In this disclosure, the various embodiments are described with reference to the flowchart illustrations and/or block diagrams of methods, apparatus (systems), and computer program products. Those skilled in the art would understand that each block of the flowchart illustrations and/or block diagrams, and combinations of blocks in the flowchart illustrations and/or block diagrams, can be implemented by computer readable program instructions. The computer readable program instructions can be provided to a processor of a general purpose computer, special purpose computer, or other programmable data processing apparatus to produce a machine, such that the instructions, which execute via the processor of the computer or other programmable data processing apparatus, create means for implementing the functions or acts specified in the flowchart and/or block diagram block or blocks. The computer readable program instructions can be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks. The computer readable program instructions can be loaded onto a computer, other programmable data processing apparatus, or other device to cause a series of operational acts to be performed on the computer, other programmable apparatus, or other device to produce a computer implemented process, such that the instructions that execute on the computer, other programmable apparatus, or other device implement the functions or acts specified in the flowchart and/or block diagram block or blocks.

In this disclosure, the block diagrams in the Figures illustrate the architecture, functionality, and operation of possible implementations of systems, methods, and computer program products according to the various embodiments. Each block in the flowchart or block diagrams can represent a module, segment, or portion of instructions, which comprises one or more executable instructions for implementing the specified logical function(s). In some embodiments, the functions noted in the blocks can occur out of the order noted in the Figures. For example, two blocks shown in succession can, in fact, be executed concurrently or substantially concurrently, or the blocks can sometimes be executed in the reverse order, depending upon the functionality involved. In some embodiments, each block of the block diagrams and/or flowchart illustration, and combinations of blocks in the block diagrams and/or flowchart illustration, can be implemented by a special purpose hardware-based system that performs the specified functions or acts or carry out combinations of special purpose hardware and computer instructions.

In this disclosure, the subject matter has been described in the general context of computer-executable instructions of a computer program product running on a computer or computers, and those skilled in the art would recognize that this disclosure can be implemented in combination with other program modules. Generally, program modules include routines, programs, components, data structures, etc. that perform particular tasks and/or implement particular abstract data types. Those skilled in the art would appreciate that the computer-implemented methods disclosed herein can be practiced with other computer system configurations, including single-processor or multiprocessor computer systems, mini-computing devices, mainframe computers, as well as computers, hand-held computing devices (e.g., PDA, phone), microprocessor-based or programmable consumer or industrial electronics, and the like. The illustrated embodiments can be practiced in distributed computing environments where tasks are performed by remote processing devices that are linked through a communications network. Some embodiments of this disclosure can be practiced on a stand-alone computer. In a distributed computing environment, program modules can be located in both local and remote memory storage devices.

In this disclosure, the terms "component," "system," "platform," "interface," and the like, can refer to and/or include a computer-related entity or an entity related to an operational machine with one or more specific functionalities. The disclosed entities can be hardware, a combination of hardware and software, software, or software in execution. For example, a component can be a process running on a processor, a processor, an object, an executable, a thread of execution, a program, and/or a computer. By way of illustration, both an application running on a server and the server can be a component. One or more components can reside within a process and/or thread of execution and a component can be localized on one computer and/or distributed between two or more computers. In another example, respective components can execute from various computer readable media having various data structures stored thereon. The components can communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As another example, a component can be an apparatus that provides specific functionality through electronic components without mechanical parts, wherein the electronic components can include a processor or other means to execute software or firmware that confers at least in part the functionality of the electronic components. In some embodiments, a component can emulate an electronic component via a virtual machine, e.g., within a cloud computing system.

The phrase "application" as is used herein means software other than the operating system, such as Word processors, database managers, Internet browsers and the like. Each application generally has its own user interface, which allows a user to interact with a particular program. The user interface for most operating systems and applications is a graphical user interface (GUI), which uses graphical screen elements, such as windows (which are used to separate the screen into distinct work areas), icons (which are small images that represent computer resources, such as files), pull-down menus (which give a user a list of options), scroll bars (which allow a user to move up and down a window) and buttons (which can be "pushed" with a click of a mouse). A wide variety of applications is known to those in the art.

The phrases "Application Program Interface" and API as are used herein mean a set of commands, functions and/or protocols that computer programmers can use when building software for a specific operating system. The API allows programmers to use predefined functions to interact with an operating system, instead of writing them from scratch. Common computer operating systems, including Windows, Unix, and the Mac OS, usually provide an API for programmers. An API is also used by hardware devices that run software programs. The API generally makes a programmer's job easier, and it also benefits the end user since it generally ensures that all programs using the same API will have a similar user interface.

The phrase "central processing unit" as is used herein means a computer hardware component that executes individual commands of a computer software program. It reads program instructions from a main or secondary memory, and then executes the instructions one at a time until the program ends. During execution, the program may display information to an output device such as a monitor.

The term "execute" as is used herein in connection with a computer, console, server system or the like means to run, use, operate or carry out an instruction, code, software, program and/or the like.

In this disclosure, the descriptions of the various embodiments have been presented for purposes of illustration and are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein. Thus, the appended claims should be construed broadly, to include other variants and embodiments, which may be made by those skilled in the arts.

What is claimed is:

1. A system for the real-time monitoring and updating of a prediction of concrete drying, the system comprising:
    one or more sensors positioned inside a concrete slab and one or more sensors positioned outside the concrete slab, each of the one or more sensors positioned inside and outside the concrete slab to transmit data to a cloud-based web portal configured to transmit a prediction to a computing device.

2. The system of claim 1, further comprising an algorithm operated by the cloud-based web portal, the algorithm to receive the data and calculate the prediction.

3. The system of claim 1, wherein the data is comprised of the following: relative temperature inside the concrete slab, relative humidity outside the concrete slab, temperature inside the concrete slab, temperature outside the concrete slab.

4. The system of claim 2, wherein the data further comprises a date and a time when the concrete slab was poured, and a target relative humidity value inside the concrete slab.

5. The system of claim 1, wherein the algorithm performs the following steps:
    filtering instantaneous relative humidity from inside the concrete slab;
    calculating absolute humidity values in the concrete slab from the respective relative humidity and temperature values;
    applying a non-linear extrapolation curve on the filtered relative humidity values from inside the concrete slab;
    adjusting the extrapolation curve with a factor calculated from the difference of absolute humidity inside and outside the concrete slab to provide a prediction to the computing device.

6. The system of claim 1, wherein a user inputs a time at which the concrete slab was cast.

7. The system of claim 1, wherein the algorithm is self-adjusting.

8. A method for the rea I-time monitoring and updating of a prediction of concrete drying, the method comprising the steps of: filtering instantaneous relative humidity from inside a concrete slab; calculating absolute humidity values in the concrete slab from the respective relative humidity and at least one temperature value; applying a non-linear extrapolation curve on the filtered relative humidity values from inside the concrete slab; and adjusting the extrapolation curve on one or more filtered relative humidity values from inside the concrete slab.

9. The method of claim 8, further comprising one or more sensors positioned inside the concrete slab and one or more sensors positioned outside the concrete slab.

10. The method of claim 9, wherein each of the one or more sensors positioned inside the concrete slab is operable to transmit data to a cloud-based web portal.

11. The method of claim 10, wherein the cloud-based web portal is operable to transmit a prediction to a computing device.

12. The method of claim 11, further comprising an algorithm operated by the cloud-based web portal, the algorithm to receive the data and calculate the prediction.

13. The method of claim 12, wherein the data is comprised of the following: relative temperature inside the concrete slab, relative humidity outside the concrete slab, temperature inside the concrete slab, temperature outside the concrete slab.

14. The method of claim 13, wherein the data further comprises a date and a time when the concrete slab was poured, and a target relative humidity value inside the concrete slab.

15. The method of claim 14, wherein a user inputs a time at which the concrete slab was cast.

16. The method of claim 15, wherein the algorithm is self-adjusting.

17. The method of claim 16, further comprising the step of notifying, via the user, a group to perform a next construction phase.

* * * * *